United States Patent [19]

Singleton

[11] Patent Number: 4,807,625
[45] Date of Patent: Feb. 28, 1989

[54] MEMBRANE PUNCTURING ASPIRATOR WITH DRAINAGE SHIELD

[76] Inventor: Rosa R. Singleton, 3106 Edgewood Ave., Richmond, Va. 23222

[21] Appl. No.: 70,588

[22] Filed: Jul. 7, 1987

[51] Int. Cl.$^4$ ............................................. A61B 17/42
[52] U.S. Cl. ............................... 128/361; 128/329 R; 604/45; 604/55
[58] Field of Search .................. 128/329 R, 361, 753, 128/754; 604/33, 36, 40, 45, 46, 48, 55, 272–274, 276–278, 902, 115

[56] References Cited

U.S. PATENT DOCUMENTS

| | | | |
|---|---|---|---|
| 2,195,771 | 4/1940 | Estler | 604/355 |
| 3,096,764 | 7/1963 | Uddenberg | 604/278 |
| 3,896,810 | 7/1975 | Akiyama | 604/117 |
| 4,662,376 | 5/1987 | Belanger | 128/361 |
| 4,692,140 | 9/1987 | Olson | 604/40 |

*Primary Examiner*—C. Fred Rosenbaum
*Attorney, Agent, or Firm*—Cushman, Darby & Cushman

[57] ABSTRACT

An obstetretic aspirator device for puncturing amniotic membranes and draining fluids therefrom comprising a funnel-shield (20) serving as a drainage cup and fluid confinement shield and puncture-type tubular aspirator (10) slideable mounted within an elongated shaft (24) of the funnel-shield for puncturing the amniotic membrane. The inner funnel wall (21) of the funnel-shield includes a plurality of suction ports (22) for draining fluids. A common vacuum source connected to the discharge end (18) of the tubular aspirator (10) communicates with both the tubular aspirator (10) and the funnel-shield (20) through the mating openings. The tubular aspirator (10) can be separated from the assembly for sole use as a conventional aspirator. The funnel-shield (20) comprises a pair of spaced apart superposed funnels walls (21 and 23) having a vacuum chamber (27) therebetween which chamber communicates with a vacuum chamber of the tubular aspirator through mating openings (19 and 25). In use, the funnel-shield is placed over the female peritoneal region and puncture-type tubular aspirator (10) is driven forwardly to puncture the amniotic sac whereby amniotic fluids are both confined to an area within the mouth of the funnel-shield and drained by the suction ports contained in the funnel-shield.

5 Claims, 2 Drawing Sheets

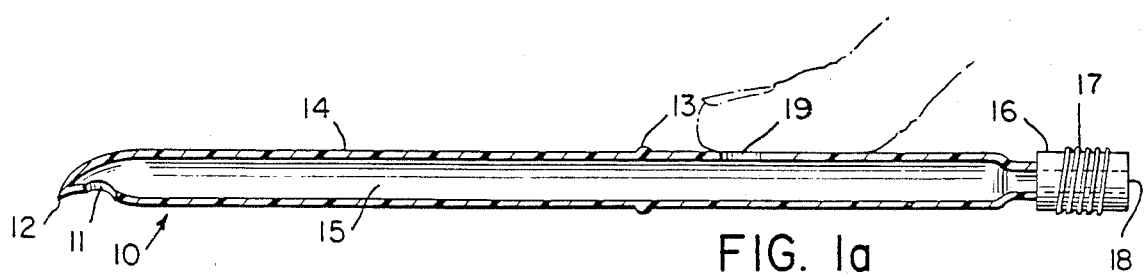
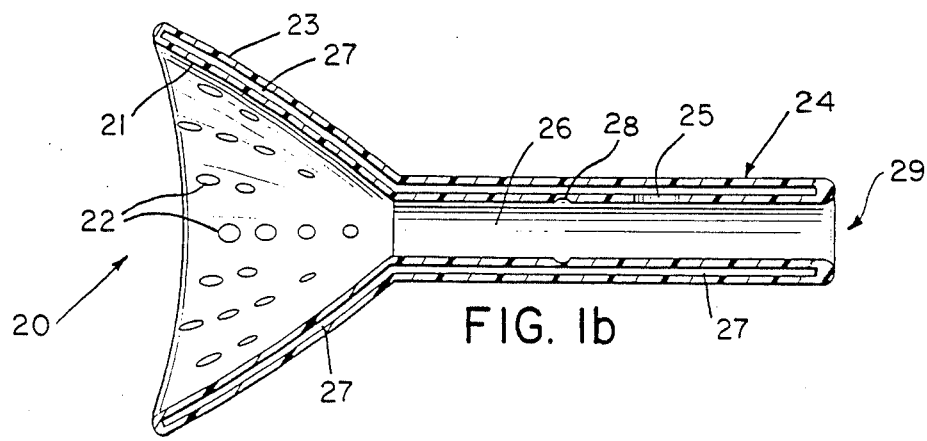
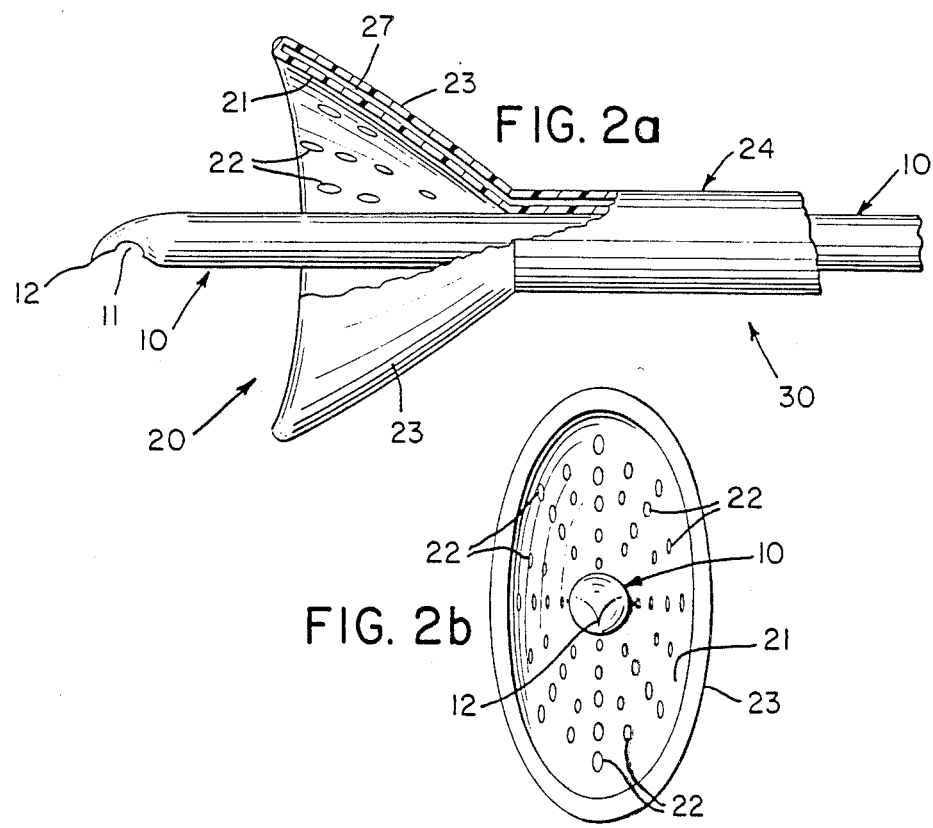

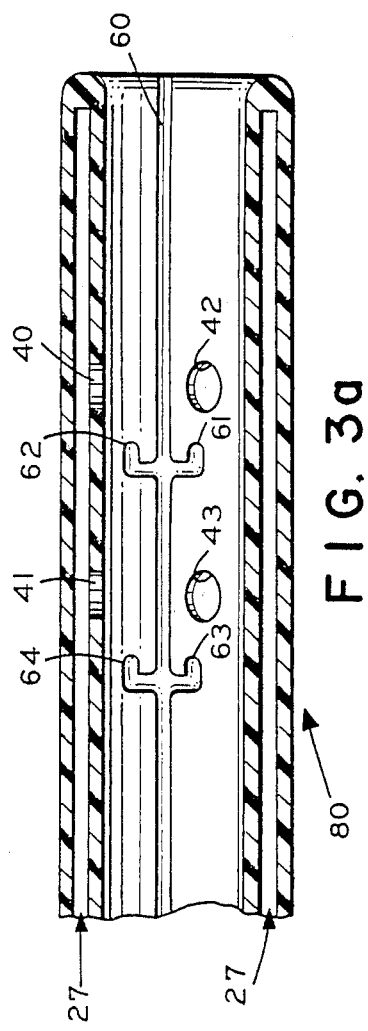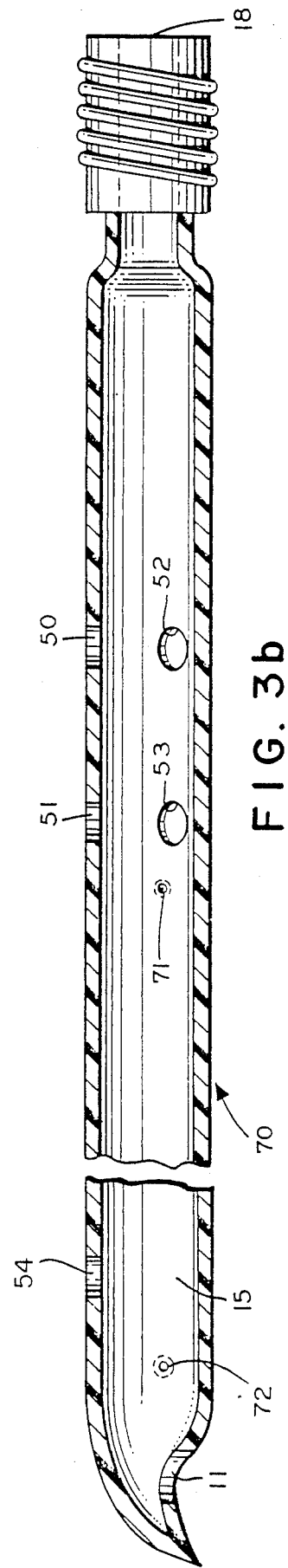
FIG. 3a
FIG. 3b

MEMBRANE PUNCTURING ASPIRATOR WITH DRAINAGE SHIELD

BACKGROUND OF THE INVENTION

1. Field of Invention

This invention relates to medical devices and more specifically to vacuum aspirators for use in draining amniotic fluids in preparation of delivery of newborn children.

2. Description of Prior Arts

Before delivery of a child, an obstetrician must rupture the amniotic membrane and remove the fluids contained therein. This membrane embraces the baby while it resides in the womb of the mother. Once the membrane is ruptured, most of the fluid can be removed by aspiration and the remaining fluid might be absorbed by sponges and towels. Because the fluid is retained under slight pressure, it sometimes flows about the patient and delivery personnel and thus may hamper normal delivery efficiency. Thus, it is desired to minimize or eliminate flowing of, and conveniently drain and dispose of the fluids.

One device suitable for aspirating fluids is described in U.S. Pat. No. 2,195,771 issued to Estler which shows a suction drainage cup for irrigating the substance of a wound. The device comprises a rigid cup-like structure having spaced walls that form a chamber therebetween communicating with a vacuum source. When the drainage cup is placed over a wound, any fluid substance captured by the cup is aspirated through a plurality of drainage ports located about the lip of the inner wall of the drainage cup.

A similar device, at least in the sense of aspirating fluids, is described in U.S. Pat. No. 3,896,810 issued to Akiyama on July 29, 1975. It is specifically adpated to aspirate fluids of cystic tumors and comprises a cup-like vacuum chamber for holding in place the tissue surrounding the tumor. A tubular aspirator having a coaxial drainage tube extends through the cup-like vacuum chamber. The drainage tube also has a sharp cutting edge on the end thereof which is used to puncture the cyst. In its operation, vacuum pressure holds the tissue in place while a physician manually drives the tube so that its cutting edge punctures the cyst. The cyst is then drained through the drainage tube.

While these devices are suitable for their respective applications, there is sometimes a need to perform simultaneously both vacuum aspiration and puncturing while, at the same time, shielding the patient and delivery personnel from the fluid substance.

In view of the foregoing, it is an object of this invention to provide an aspirator and shield assembly serving those combined functions, the components of which may be used separately or together, and wherein each component performs an aspirating function.

It is another object of the invention to provide an aspirator assembly useful for aspirating amniotic fluids during childbirth operations whereby an amniotic membrane can be punctured and the fluids contained therein can be confined within the aspirator assembly and then vacuum aspirated without splashing thereof about the patient.

It is another object of the invention to provide an aspirator assembly adaptable to a variety of configurations so as to perform a variety of different aspirating functions.

Other advantages, objects and features of the invention will become apparent upon review of the succeeding disclosure taken in connection with the accompanying drawings.

SUMMARY

In accordance with the invention, an aspirator-shield device comprises two components wherein the vacuum chamber of each component communicates with a common vacuum source. The combination includes a tubular aspirator subassembly that is inserted into a shaft of a funnel-shield aspirating component. The tubular aspirator is hollow and carries fluids. The funnel-shield comprises spaced walls which also define a hollow aspirating chamber therebetween which carries fluids. At least one opening in the shaft of the funnel-shield can be moved into alignment with at least one corresponding opening in the tubular aspirator so that, by sliding and rotating the tube within the shaft, the common vacuum source can supply the chambers of both the tubular aspirator and funnel-shield.

In assembled reaction, a small stud on the outer surface of the tubular aspirator mates with a guiding track, or grooove, disposed on the inner surface of the shaft of the funnel-shield so that the respective openings can be moved into alignment. In an alternative embodiment of the invention, a plurality of openings in both the shaft of the funnel shield and the tubular aspirator are provided thereby providing means to regulate the level of vacuum aspiration by aligning a variable number of respective openings.

In the preferred embodiment, the aspirator-shield and the tubular aspirator are constructed of a transparent plastic or rubber-like material so that their chambers may be visually inspected. Different portions of the device may have a rigidity corresponding to the need to withstand forces associated with the negative aspirating pressure, contact with the patient, handling by the obstetrician, or interaction between the respective components. Specifically, the walls of the funnel-shield and the tubular aspirator are of sufficient rigidity so as to not collapse under negative pressure provided by the common vacuum source. The mouth of the funnel-shield which contacts the patient is of sufficient rigidity to withstand negative pressure of the vacuum source without collapsing but yet is soft enough to provide patient comfort. The neck of the funnel-shield and the tubular aspirator are sufficiently rigid for handling by the obstetrician. The contacting surfaces between the funnel-shield and tubular aspirator are wear resistant thereby to prolong its use under continuous sliding and twisting action between the tubular aspirator and the shaft of the funnel-shield. Further, the shape of the mouth of the funnel is ovoid in the axial direction and concaved from a side view, thereby to compliment the shape of the perineal-vaginal area about which the device is used.

The invention however is pointed out with particularity in the appended claims.

BRIEF DESCRIPTION OF THE DRAWINGS

FIG. 1(a) is a cross-sectional view of the tubular portion of the aspirator assembly.

FIG. 1(b) is a cross-sectional view of the funnel-shield portion of the aspirator assembly.

FIG. 2(a) is a partial cut-away side view of the aspirator in assembled relationship.

FIG. 2(b) is a front view of the aspirator assembly of FIG. 2(a).

FIG. 3(a) is a cut-away of the neck of the funnel-shield shown in FIG. 1(a).

FIG. 3(b) is a cross-sectional view of another of the tubular portion of the aspirator that can be inserted in the neck shown in FIG. 3(a).

DESCRIPTION OF AN ILLUSTRATIVE EMBODIMENT

FIGS. 1(a) and 1(b) respectively depict the tubular aspirator 10 and funnel-shield 20. The tubular aspirator 10 may be used solely, just as a conventional aspirator, or it may be used in conjunction with the funnel-shield as will be subsequently explained. The aspirator 10 comprises a hollow tube 14 having at one end thereof a suction port 11 for aspirating fluids together with a sharp needle-like puncture point 12 suitable for puncturing membranes. A drainage port 18 is located at the other end of the aspirator 10. A vacuum source (not shown) communicates via a conduit 16 with an internal chambers 15 of the tubular aspirator 10. The vacuum source provides sufficient negative pressure in a chamber 15 so that amniotic fluids can be drawn into the suction port 11 to a discharge reservoir coupled with the conduit 16. The material from which the tube 14 and the funnel aspirator 20 may, for example, be plastic or rubber. The mouth of the funnel-shield 20 is somewhat more resilient than the remaining portion thereby to provide patient comfort during use. The walls of both tubular aspirator 10 and the funnel-shield 20 are rigid enough to withstand the forces tending to collapse them due to the negative pressure created by the vacuum source. Constructing the device of a transparent material, such as plastic, would aid obstetricians in visually observing the fluid flow during aspiration.

The level of negative pressure, and consequently the aspirating rate of the fluids, can be controlled by positioning the thumb to control the effective area of an optional relief port 19 disposed on the wall of the tube 14. In operation, an obstetrician would hold the tube 10 in his hand while his thumb is placed over the relief port 19. By manually positioning the thumb over different areas of te relief port 19, the level of negative pressure, or the aspirating rate, at suction port 11 can be varied. This provides a quick and convenient method for adjusting the aspiration pressure. Ordinarily, the obstetrician must adjust the pressure level at the vacuum source which would take away needed attention for aspirating fluids and observing the patient.

The funnel-shield 20 of FIG. 1(b) comprises a cup-like multiported aspirating head which is concave inwardly as shown from the side view. The concave shape conforms to the contour of the female peritoneal area about which the device is used. FIG. 2(b) depicts the head in front view where the shape is shown to be ovoid from an axial direction. The extent of concavity of the head of the funnel 20 and its oval shape may be varied somewhat to more precisely complement the area of use.

To aspirate fluids, the funnel-shield 20 of FIG. 1(b) includes a plurality of suction ports 22 extending through its inner wall 21. These suction ports 22 communicate with a vacuum chamber 27 defined by the inner wall 21 and an outer wall 23. The outer wall 23 has no ports. The inner wall 21 and the outer wall 23 are joined at both the periphery of the mouth of the funnel and at the end 29 of the shaft 24 thereby to define a chamber 27 therebetween. Spacers could also be employed to keep separated in spaced relation the inner and outer walls 21 and 23 under negative pressure, or a number of channels or hollow tubes in a solid wall could constitute the path of fluid drainage from the suction ports to the vacuum source. An opening 25 in the internal wall of the shaft 24 provides the means by which the vacuum chamber 27 acquires negative pressure when it is coupled together with the tubular aspirator 10 in a fashion to align opening 19 on tube 10 with the opening 25. In the embodiment shown, the funnel-shield 20 is used with the tubular aspirator 10 being inserted into its cavity 26 so that it assumes the relative positions as shown in FIG. 2(a). In such configuration, the vacuum source provides negative aspirating pressure for both the tube 10 and the funnel-shield 20.

To use the assembly solely as a drainage cup, the tubular aspirator 10 is retracted rearwardly of the mouth of the funnel-shield 20 so that the sharp puncturing edge 12 resides within the shaft 24 and thus prevents inadvertent contact of the puncturing edge with the patient.

FIGS. 3(a) and 3(b) depict further details of the tubular aspirator and the neck of the funnel shield portion, which details illustrate the means for providing different vacuum levels using a constant level vacuum source. The aspirating rate then is regulated by the relative positioning between the tube 10 and shaft 80. For instance, when the separate components are mated, the groove 60 that is cut into the inner surface of the shaft 80 of the funnel-shield guides the tubular aspirator 10 via stud 71 by twisting or sliding action of the tube 10. To attain a first position, the stud 71 slides along the groove 60 upon longitudinal displacement of the tube 70 so that openings 50, 51, 52 and 53 are aligned with openings 40, 41, 42, and 43 when inserted and twisted clockwise, in which case, stud 71 rests at inset 63. When the stud 71 is positioned to rest in the inset 61, openings 53 and 51 are aligned with openings 42 and 40, respectively. In this manner, the total area with which the vacuum chamber 15 communicates with the vacuum chamber 27 can be varied thereby to regulate the level of negative pressure at the suction ports 11 and 22.

When the tubular aspirator 70 is retracted into the neck of the funnel, a second stud 72 can be positioned in groove 60 at one of the insets 63 or 61 thereby to align an opening 54 of the tube 70 with openings 41 or 40 of the neck 80. The funnel-shield 20 then serves as a drainage cup. A variety of other configurations of grooves, studs, and insets can be employed by those persons skilled in the art to provide other relative positions of the tube 70 and neck 80 of the funnel-shield, or different negative pressures in the chamber 27 of the funnel-shield. One aspect of my invention though broadly includes the provision of studs, grooves, insets, and openings so that different levels of negative pressures can be attained.

In view of the foregoing, the illustrated embodiments are not considered to be a limitation of the scope of the invention. It is my intent to include all such modifications and arrangements that are within the perception of one skilled in the art to which this subject matter pertains.

Now, therefore, a brief description having been made, what is claimed is as follows:

1. A funnel-shaped aspirating device for aspirating a region of a patient, said device comprising:
   a funnel-shield including a mouth, a shaft, and a chamber between the inner and outer spaced-apart walls for aspirating fluids, a plurality of suction ports disposed in the inner wall of said funnel-shield communicating with said chamber, and at least one opening in the inner wall of said shaft of the funnel-shield for communicating with a source of negative pressure, the mouth of said funnel-shield being anatomically contoured to mate with the lower uterine segment of a patient, said funnel-shield being transparent in at least a portion thereof to permit visual observation of the region of aspiration; and a tubular aspirator means having a puncture end and a discharge end, said tubular aspirator means comprising an elongated hollow shaft adapted to be slideably circumcased within the shaft of said funnel-shield, said tubular aspirator means including at the puncture end thereof a membrane puncture means and a fluid inlet port, said tubular aspirator means having at least one relief port therein for communicating with a common vacuum source that supplies negative aspirating pressure to both said funnel-shield and said tubular aspirator means when said relief port on the tubular aspirator means and the opening in the inner shield shaft are in alignment.

2. An aspirating device as recited in claim 1 further including:
stud means and guide track means located between said tubular aspirator means and funnel-shield for fixedly positioning said tubular aspirator in a position so that the puncture end protrudes beyond the mouth of said funnel-shield while at least one set of respective openings between said aspirator means and funnel-shield are in alignment.

3. A funnel-shaped aspirating device as recited in claim 1 further including thumb controlled relief port disposed on said tubular aspirator for controlling the source of negative pressure applied to said funnel-shield and said tubular aspirator.

4. A funnel-shaped aspirating device as recited in claim 1 wherein the mouth of said funnel-shield has an ovoid shape in order to mate the anatomical region of the patient.

5. A funnel-shaped aspirating device as recited in claim 1 wherein the size of said plurality of suction ports are adapted for aspirating amniotic fluids without clogging by extraneous substances contained therein.

* * * * *